(12) United States Patent
Dunfee et al.

(10) Patent No.: US 6,370,942 B1
(45) Date of Patent: Apr. 16, 2002

(54) METHOD FOR VERIFYING THE INTEGRITY OF A FLUID TRANSFER

(75) Inventors: William David Dunfee, New Castle, DE (US); Kerry Lynn Miller, Elkton, MD (US)

(73) Assignee: Dade Behring Inc., Deerfield, IL (US)

( * ) Notice: Subject to any disclaimer, the term of this patent is extended or adjusted under 35 U.S.C. 154(b) by 0 days.

(21) Appl. No.: 09/570,639

(22) Filed: May 15, 2000

(51) Int. Cl.[7] ............... G01N 1/00; G01N 35/00; G01B 13/00
(52) U.S. Cl. ............... 73/37; 73/1.74; 73/40; 73/63.01; 73/864.14; 73/864.25; 73/436; 73/148
(58) Field of Search ............... 73/864.11, 864.15, 73/37, 40, 40.5 R, 1.05, 1.36, 1.58, 1.68, 1.73, 1.74, 863.01, 864.25, 864.14, 864.24; 436/148; 702/51, 81, 82, 182, 183; 422/923

(56) References Cited

U.S. PATENT DOCUMENTS

| | | | |
|---|---|---|---|
| 4,280,356 A | * | 7/1981 | Stewart .................. 73/40.5 R |
| 4,675,301 A | | 6/1987 | Charneski et al. .......... 436/180 |
| 4,715,214 A | * | 12/1987 | Tveter et al. .................. 73/40 |
| 5,451,373 A | | 9/1995 | Lewis et al. ............. 422/82.13 |
| 5,463,895 A | | 11/1995 | Brentz ....................... 73/61.71 |
| 5,488,874 A | | 2/1996 | Kawanabe et al. ...... 73/863.01 |
| 5,503,036 A | | 4/1996 | Nguyen et al. .......... 73/864.34 |
| 5,537,880 A | | 7/1996 | Takeda et al. ........... 73/864.25 |
| 5,540,081 A | | 7/1996 | Takeda et al. ................. 73/37 |
| 5,622,869 A | | 4/1997 | Lewis et al. ................. 436/148 |
| 5,814,275 A | | 9/1998 | Lewis et al. .................. 422/63 |
| 6,016,690 A | * | 1/2000 | Cook et al. ............. 73/40.5 R |
| 6,022,747 A | | 2/2000 | Gherson et al. .............. 436/69 |
| 6,060,320 A | | 5/2000 | Dorenkott et al. ............. 436/54 |
| 6,121,049 A | * | 9/2000 | Dorenkott et al. ............. 73/37 |

* cited by examiner

Primary Examiner—Hezron Williams
Assistant Examiner—Michael Cygan
(74) Attorney, Agent, or Firm—Leland K Jordan

(57) ABSTRACT

A liquid aspiration method which includes a method for determining the quality of the aspirated sample through mathematical analysis of the pressure profile generated before, during, and after the aspiration process and comparison of the results with predetermined known values.

4 Claims, 8 Drawing Sheets

METHOD FOR VERIFYING THE INTEGRITY OF A FLUID TRANSFER

FIELD OF THE INVENTION

The presen invention relates to the transfer of an amount of liquid from one container to another, and more particularly, to a method for ascertaining the overall quality and integrity of a liquid aspiration process using a vacuum actuated pipette.

BACKGROUND OF THE INVENTION

Fully automated diagnostic analyzers are commercially available to perform chemical assays and immunoassays of biological fluids such as urine, blood serum, plasma, cerebrospinal liquids and the like. Generally, reactions between an analyte in a patient sample and reagents used during the assay, result in generating some sort of signal that can e measured by the analyzer. From this signal the concentration of analyte in the patient sample may be calculated. Such automated analyzers generally use an aspirating means such as a sampling tip, or probe or needle, to transfer predetermined volumes of liquid samples or liquid reagents between receptacles, such as between sample containers, reagent containers and reaction cuvettes disposed on the analyzer. Hereinafter, variations of the term aspirate refer to all of such processes for extracting liquid from one container and depositing at least some of the liquid into the same or another container and further includes the supporting devices required to complete the liquid handling operations.

Aspirator are typically employed for transporting liquids between reservoirs which hold liquid samples and/or reagents and for transporting liquids from such reservoirs to test sites such as in assay cuvettes or cartridges to conduct various tests. The aspirating means typical includes an elongated, needle-like member called a pipette having a hollow passage whereby liquid may be aspirated into and/or dispensed from the sample probe using appropriate pumping resources. The pipette is carried by a transport mechanism adapted to provide horizontal and vertical movement so as to enable the pipette tip to be lowered into a liquid in a reservoir for aspiration of the liquid, and for transporting the liquid to a test site whereat the pipette is lowered to an optimal position for dispensing the liquid. Some type of device, such as a piston assembly, which may be incorporated into the pipette, is operated electronically to aspirate liquid into the pipette and to dispense liquid from the pipette.

It is desirable, when aspirating liquid, to accurately determine the extent any abnormalities or non-uniformities within the liquid adversely affect the overall quality of the aspiration process. Non-uniformities such as clots, bubbles, foam, insufficient volume, etc, are found in many liquids, particularly when the liquid is one of several body fluids being analyzed as these frequently are of non-uniform composition. Various methods have been developed to detect the effect of such non-uniformities on the aspiration process.

U.S. Pat. No. 6,022,747 discloses a blood clot detector having a pressure transducer on an aspiration line to provide output voltage data to a microprocessor corresponding to the vacuum level during aspiration. The microprocessor integrates the vacuum readings over time during the aspiration cycle to provide a pressure integral for each test sample aspiration. A pressure integral is determined for an unclotted aspiration and is used as a reference for comparison with the pressure integrals of each test sample aspiration to determine whether a blood clot has interfered with the test sample aspiration. A valve is provided across an analytical line and an aspiration line to provide selective communication between the aspiration line and the analytical line or to prevent such communication. Communication between the aspiration line and the analytical line permits transfer of a test sample from the aspiration line to the analytical line if the test sample is considered acceptable for sample analysis. Acceptability of the test sample for analysis is based upon a predetermined difference between the reference pressure integral and each test sample pressure integral.

U.S. Pat. Nos. 5,814,275, 5,622,869 and 5,451,373 relate to an apparatus for detecting obstructions of a flow line. A detector housing has first and second openings into a cavity therein. The flow line is attached to the detector housing establishing a flow path through the first opening, the cavity, and the second opening, respectively. A pressure detector detects changes in pressure within the cavity, indicating the presence of an obstruction. A rigid barrier is disposed near the pressure detector on a side of the pressure detector opposite the flow line, so that when said flow line and pressure detector expand, the rigid barrier does not expand and the pressure detector is compressed.

U.S. Pat. No. 5,540,081 relates to a pipetting apparatus provided with clot detection comprising a nozzle for aspirating a sample. A pressure sensor is connected with the nozzle for measuring pressure in said nozzle. A plurality of pressure difference calculating circuits are connected with the pressure sensor, each for inputting an output of the pressure sensor and obtaining a pressure difference at a different pressure calculation period. A plurality of discriminating circuits each having a different discrimination threshold value determined according to each of the pressure calculation periods are provided. An alarm circuit is included for outputting a clot detection alarm signal when at least one of said discriminating circuits discriminates that the obtained pressure difference exceeds the discrimination threshold value.

U.S. Pat. No. 5,503,036 relates to an obstruction detection circuit for detecting an obstruction of a sample probe of an automated fluid sample aspiration/dispensation device and a method for detecting such an obstruction. In one embodiment, the obstruction detection circuit includes a pressure sensor measuring the pressure in a fluid conduit connecting a pump and to a sample probe orifice. The pressure within the connecting fluid conduit is measured shortly after the start of the aspiration or dispensation of a sample volume by the automated fluid sample aspiration-dispensation device. The pressure within the connecting fluid conduit is again measured after the completion of the aspiration or the dispensation by the pump, and if the pressure has not returned to a predetermined range within a predetermined amount of time, an error condition is reported.

U.S. Pat. No. 5,463,895 discloses provides an apparatus and method of detecting non-homogeneity in a fluid sample, such as the presence of foam or bubbles on the surface of the sample, and/or the presence of clots on the surface or in the bulk of the sample. This method involves determining the ambient air pressure within a pipettor as a baseline reading, aspirating air into the pipettor as the pipettor moves towards a sample in container and monitoring for a pressure change in the pipettor to indicate the surface level of the fluid in said container. The pipettor is immersed in the fluid and a volume of fluid is withdrawn from the container; pressure changes are monitored after aspiration and compared to predetermined normal aspiration pressure windows.

Such prior art liquid aspiration processes are not satisfactory in all instances. For example, most known systems for determining the quality or integrity of an aspiration process depend on measuring only differences in vacuum pressure at different intervals during the aspiration process and comparing these measurement to a range of predetermined satisfactory values. Accordingly, as the state of the art advances and more demands are made on the analyzer's systems there is a continuing need for liquid aspiration systems that are capable of determining additional information defining the overall quality of the aspiration process. In addition, it is useful to know if the integrity of the aspiration means is defective, for instance, as the result of an unwanted air leak.

SUMMARY OF THE INVENTION

It is therefore an object of this invention to provide a liquid aspiration method which is capable of determining the overall quality and integrity of the amount of liquid which has been aspirated into a pipette tip. This and other advantages are accomplished in accordance with the invention by providing a liquid aspiration method which includes a method for determining the quality of the aspirated sample through analysis of the pressure profile generated before, during, and after the aspiration process. Sensed aspiration pressure data used for verification of the overall quality of the aspiration process are recorded for each sample aspiration and analyzed immediately following the aspiration event. Pumping resource motion is started a specified number of reads after data collection has started. The present aspiration method checks the aspiration for undesirable events such as partial or complete clogs, or aspiration of air by employing three separate aspiration tests including a pressure difference test to verify liquid was aspirated, a pressure recovery test to check for clogs and aspiration of unwanted cells, and a pressure shape test to check for abnormalities during aspiration, such as clogs, air aspiration, density changes (due to aspiration of blood cells), etc. Three algorithms are employed, and each must produce a positive result for the sample to be released for transfer elsewhere.

BRIEF DESCRIPTION OF THE DRAWINGS

For a better understanding of the invention as well as other objects and further features thereof, reference is made to the following detailed description of various preferred embodiments thereof, taken in connection with the accompanying drawings wherein.

DETAILED DESCRIPTION OF THE PREFERRED EMBODIMENTS

Figure 1:
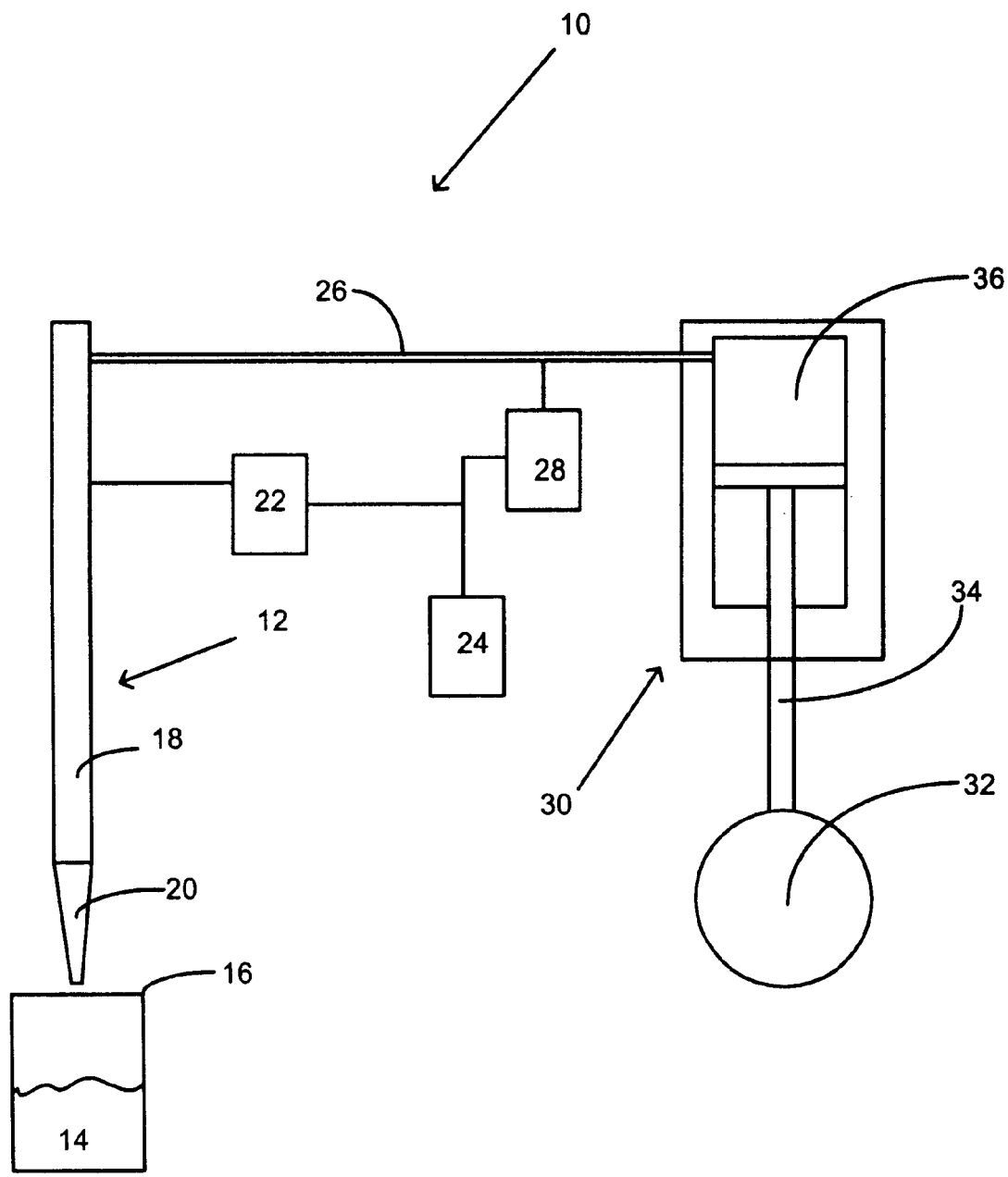
FIG. 1 is a schematic representation of an aspiration system in which the present invention may be practiced.

Referring to FIG. 1, there is illustrated a liquid aspiration system 10 according to the invention which includes a pipettor 12 for aspirating and dispensing liquid such as a sample liquid 14 stored in a reservoir 16. Although one such sample liquid 14 is shown for the purpose of describing the liquid dispensing system 10, it will be apparent to those skilled in the art that any number of sample liquid reservoirs can be present in an automated clinical analyzer. In an exemplary embodiment, the liquid aspiration system 10 may be used in an automated clinical analyzer (not shown). Such automated clinical analyzers are well known in the art and those skilled in the art will know with certainty the functions of the elements of the analyzers to which reference is made.

The pipettor 12 includes a central cavity 18 which is adapted to carry a pipette tip 20 which may have a conically narrowing nose shape terminating in a distal orifice through which liquid is aspirated into the cavity 18, and through which liquid is dispensed therefrom. The holder has a central chamber which opens into the tip cavity upon engagement of the holder with the tip. The pipette further comprises a piston assembly connecting with the holder on a top side thereof, opposite the tip. A piston in the piston assembly extends into the holder chamber.

The liquid dispensing system 10 typically include a transport device 22, indicated diagrammatically, which may be of any suitable type. The transport device 22 is capable of moving the pipettor 12 laterally (the X-direction), vertically (the Z-direction) and from front to back (the Y-direction) in an analyzer to enable the pipettor 12 to pick up a pipette tip 20 (when disposable tips are used), aspirate liquid 14 into the pipette tip 20 from the sample liquid reservoir 16 and to dispense a desired amount of sample liquid to a test assay element (not shown). Generally, a stepper-motor and limit-switches are used within transport device 22 for transporting the pipettor 12 and these are interfaced to a system computer 24 adapted and programmed to practice the present invention. Alternately, the Pipettor 12 may be translated along the vertical z-axis by a rack-and-pinion drive. The pipettor itself forms the rack, and the shuttle contains the motor and pinion and the electronic controls necessary for positioning the pipettor 12. Conventional electronic drivers and interface circuits are used to interface the transport device to the computer 24.

As shown, the pipettor 12 has a cavity 18 for holding liquid 14 and a tube 26 connected therefrom to a vacuum pressure measurement device 28 and an aspiration pressure control means 30 for producing a variable vacuum pressure throughout the pipettor 12 responsive to commands from the computer 24. Such devices and sources are well know in the art. Commercially available pipettors 12 made from metals like stainless steel or plastics like polypropylene and similar materials, and tubing 26 made from vinyl, polypropylene, polyethylene, metal, etc, may used in the present invention. Pressure measurement device 28 measures air pressure within the pipettor 12 both continuously and periodically during the aspiration method of the present invention. An exemplary pressure measurement device 28 is a pressure transducer (Model SCXL004DN from SenSym, Miltipas, Calif.) and is interfaced to the computer 24 to provide a measured air pressure within tubing 26 to computer 24.

The aspiration system 10 includes means 30 for precisely controlled aspiration pressure through the pipettor 12. An exemplary aspiration pressure control means 30 is a piston-syringe device, mechanically connected to a stepper motor 32 and home limit-switches (not shown) capable of controlling the movement of the syringe piston and causing the control means 30 to aspirate and dispense air through tubing 26. The aspiration pressure control means 30 and pressure sense device 28 are electronically interfaced to computer 24 which is used to control the operation of the liquid aspiration system 10. The computer 24 also provides signals to control the movement of the pipettor 12 via transport device 22 as well as the aspiration into, and dispensing of liquid from, the pipette tip 24.

In such an instance, as illustrated in FIG. 1, means 30 comprises a piston 34 attached to motor 32 for advancing and retracting the piston 34 within a closed chamber 36. A downward movement of piston 34 tends to increase the volume of the chamber 36, thereby to create vacuum or negative air pressure within the chamber 36 which draws air from the interconnected tubing 26, cavity 18, and pipette tip 20 into the cavity 18 for aspirating liquid 14 into the pipette tip 20. Advancing the piston 36 into the chamber 36 decreases the volume of the chamber 36, thereby to provide a positive air pressure which pushes air out of the chamber 36 into the interconnected tubing 26, cavity 18, and pipette tip 20 for expelling and dispensing liquid from the pipette tip 20 via the tip orifice. Thus, the piston unit 36 provides for aspiration of liquid into, and dispensing of liquid from, the pipette tip 20.

Tubing lengths and diameters of tubing 26 are selected to provide appropriate dynamic response of the pressure system to allow for proper level sensing and aspiration checking. The length of tubing 26 between the aspiration pressure control means 30 and the pipettor 12 provides the majority of the pressure head loss in the system 10. The length of tubing between the aspiration pressure control means 30 and the pump provides sufficient pressure damping to reduce the pressure noise generating by the individual pump steps during operation of the pipettor 12.

In accordance with the present invention, the aspiration pressure control means 30 and pressure sense device 28 are controlled and analyzed by computer 24 so as to determine the quality of the aspirated sample liquid 14 through analysis of a pressure profile generated before, during, and after the aspiration process. The aspiration quality verification method has the ability to detect insufficient or excessive sample, a clogged pipette tip 20, aspiration of air or air bubbles, aspiration of a clot or other obstruction along with the sample, and aspiration of a gel or cell layer in a centrifuged sample container, among other conditions. By providing the ability to detect other aspiration errors between the extremes of a fully clogged or fully open pipette tip 20, the present invention provides additional protection against supplying an analyzer with a low quality aspirated liquid sample. This ability provides distinct advantages as analyzers and laboratories become increasingly automated, and the amount of sample inspection performed by laboratory technicians decreases. For example, this present invention will detect the aspiration of a blood clot that is not large enough to completely clog the pipette tip, but potentially large enough to clog the analyzer sample probe. Also, if a centrifuged sample tube delivered to the analyzer by the laboratory automation system has an insufficient amount of plasma or serum above the cell layer, this method will detect the aspiration of blood cells and will prevent the contaminated sample from being analyzed and producing potentially erroneous results.

The present invention is practiced by analyzing the pressure measurements from pressure sense device 28 for each sample aspiration immediately following the aspiration process. Aspiration pressure control means 30 is activated a specified number of reads after data collection by pressure measurements from pressure sense device 28 has begun. Pressure data, for instance using an A/D (analog signals converted to digital data) converter, are collected for a period long enough to capture the entire aspiration process. The pressure data are collected in real time throughout the aspiration cycle. In a typical embodiment, an analog input subsystem reads the pressure sense device at a constant rate (for example, 25 Hz) time stamping each reading and buffering the reading(s) for eventual inclusion into the aspiration data set. In parallel to the aspiration process, the pressure data are periodically transferred from the analog sub-system buffer into the aspiration data set. The aspiration data set consists of a series of time stamped pressure readings that occur before during and after the pump operation. Each process event (start of aspiration cycle, start of pump cycle, end of pump cycle & end of aspiration cycle) is marked in the data set. To achieve close coupling with process events the data are also read from the analog sub-system coincident with these events. The resultant aspiration data set then contains a multiple of time stamped pressure and event markers that allow analysis of the overall quality of the aspiration process.

Sensing of the upper surface portion of the sample liquid 14 is performed via the system 10 by sensing a rise in air pressure as the pipette tip crosses the boundary of liquid 14. This process is well known in the art and to accomplish this, the aspiration pressure control means 30 is first moved to an appropriate zero-pressure position. Then the aspiration pressure control means 30 is utilized to blow a small stream of air out through tip 20 at a constant rate. The head loss in tubing 26 between the pipette tip 20 and the aspiration pressure control means 30 causes an increase in pressure at the pressure sensing device 28. Once the airflow has stabilized (i.e., the pressure as measured by the pressure sensing device 28 increases to a steady state), a reference pressure is taken by averaging a number of reads over several seconds. Then, the pipettor 12 is descended by the transport device 22 towards the sample. When the pipette tip 20 crosses the liquid surface, air flow out of the tip 20 is restricted, and pressure in the tubing 26 begins to rise. Level detection occurs when the pressure rises a specified threshold amount above the reference level. This detection causes the aspiration pressure control means 30 and pipettor 12 motions to be halted.

Once liquid level in the reservoir 16 has been determined, sample aspiration commences. A vacuum generated by the aspiration pressure control means 30 draws the sample liquid 14 up into the pipette tip 20. At the sample time, the pipettor 12 descends to follow the level of the sample down in reservoir 16, keeping the tip 20 immersed in liquid 14. Different descent rates are used, depending on the diameter of the reservoir 16. After aspiration is completed, the pressure profile recorded during the event is examined as described hereinafter and the pipette tip 20 is retracted from the liquid sample 14. Finally, a quantity of air is aspirated into the tip 20 to move the sample liquid 14 away from the bottom of tip 20 to prevent potential drips.

Due to weight of the fluid column in the tip, along with viscosity, surface tension, pressure head loss, and other effects, a given pump volume displacement does not aspirate an equal amount of sample. However, the relationship between displaced volume and aspirated volume is known be linear and is relatively insensitive to the total air volume in the system (a 10% change in air volume results in a 1% change in delivered sample volume). Thus, by analysis, it is also insensitive to the ambient pressure.

The rate of aspiration is chosen to provide a pressure profile with the features necessary for aspiration success analysis described below while minimizing cycle time and keeping the magnitude of the pressure signal within the limits of the pressure sense device 28.

The present invention checks the aspiration process for events such as partial or complete clogs, or aspiration of air. The aspiration verification algorithm of the present invention is composed of three separate tests each performed by a separate algorithm and each must produce a positive result before the aspirated sample may be released for transfer for subsequent analysis. An error signal may be generated if any of the three tests fail to produce an acceptable result. These separate tests comprise:

A Pressure Shape test to check for abnormalities during aspiration, such as clogs, air aspiration, density changes (due to aspiration of cells), etc.

A Pressure Recovery test to check for clogs and aspiration of cells; and,

A Pressure Difference test to verify that liquid was aspirated;

The following sequence of events comprises an exemplary embodiment of the present invention using the above three separate tests:

Start pressure data measurements using vacuum pressure measurement device 28 at a predetermined rate.

Delay for a predetermined number of pressure readings.

Start aspiration or dispense using aspiration pressure control means 30.

Wait for the aspiration or dispense cycle to complete.

Delay for a predetermined number of pressure readings.

Stop pressure data collection.

Perform Pressure Shape test, described hereinafter; if successful, proceed to a Pressure Recovery test.

Perform Pressure Recovery test, described hereinafter; if successful, proceed to a Pressure Difference test.

Perform Pressure Difference test, described hereinafter.

Figure 2:
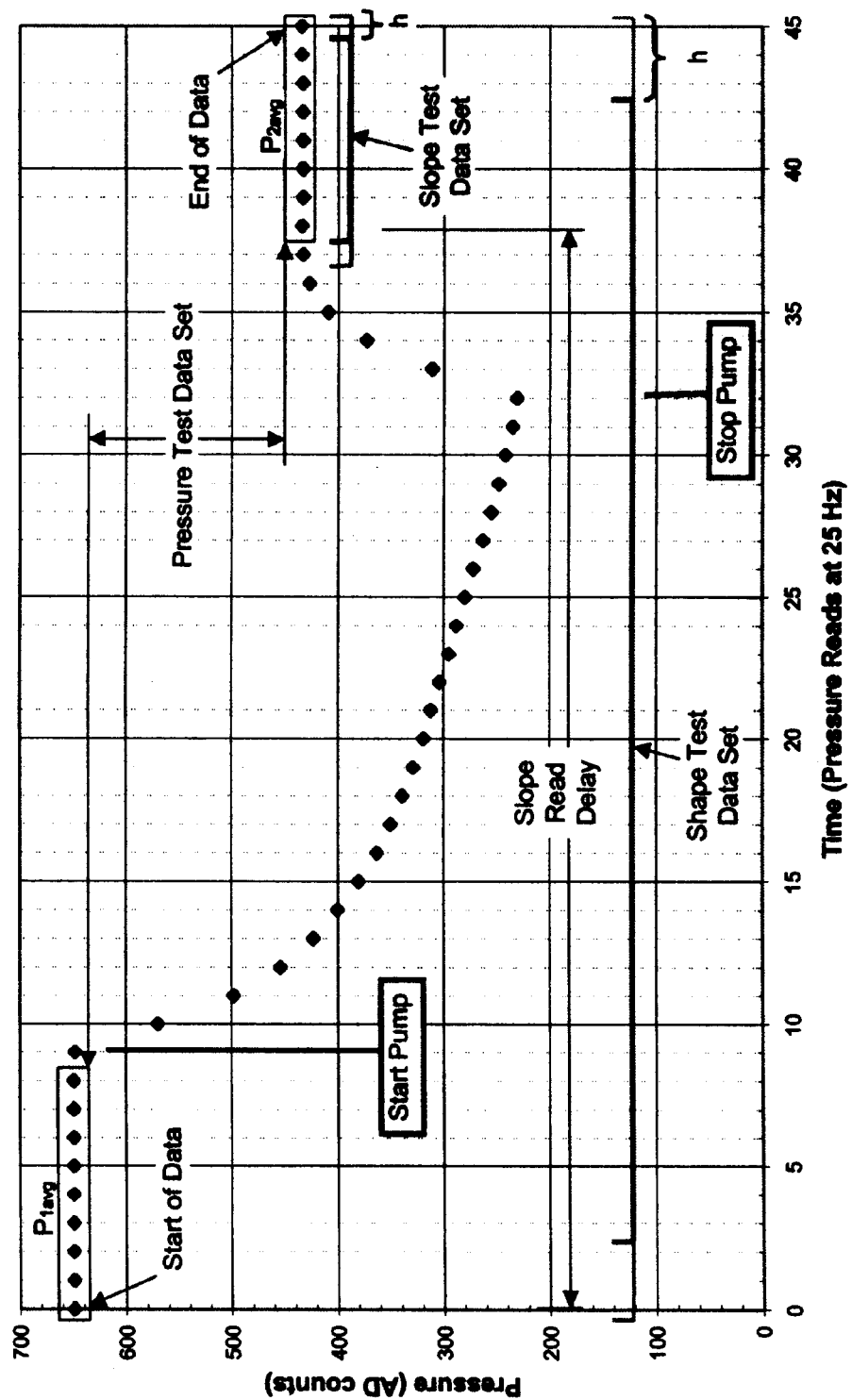
FIG. 2 is a graphical representation of aspiration pressure values illustrative of the system of FIG. 1.

It is important to note that the Pressure Shape, Pressure Recovery and Pressure Difference tests above may be performed independently or in other variations of the described manner. Each of the three tests is able to determine various aspects of the overall quality of the aspiration process. A graphical representation of the data sets used in the aspiration verification algorithms in this exemplary embodiment of the present invention is shown in FIG. 2. Since the pressure tests measure head pressure, rate of pressure change, and general curve shape, the algorithm will be relatively insensitive to altitude and other ambient-pressure-related effects. The current embodiment limits aspiration to samples with viscosity's up to 15 times that of water, and only samples up to 10 times that of water are recommended for reliable operation. Typical sample viscosity's (serum, plasma, urine, etc) range from 1 to 2 times that of water, with typical diseased samples ranging up to 5 times that of water. Samples with viscosity's greater than 15 times that of water may saturate the pressure measurement device 28, resulting in an aspiration error. Alternate pressure measurement devices could be used over other viscosity ranges. The parameters could also be set to distinguish between fluid types; for example, normal serum from whole blood. Viscosity has only a minor effect on dispensed volume, as a 10× increase in viscosity reduces the dispensed volume by about 4%.

Pressure Shape Test

The Pressure Shape test verifies that the shape of the aspiration pressure curve matches that of a good aspiration pressure curve, and thus is a measure of the uniformity of the aspiration. Sudden changes in the aspiration will be detected, such as those caused by clogs, aspiration of air, significant fluid density changes, etc.

The shape of the curve is measured by counting the number of inflection points, or points where the rate of change of the slope of the pressure curve is zero. A typical "good" aspiration pressure curve in the current embodiment is "bathtub" shaped, and thus has six inflection points:

Start of aspiration;

Midpoint of pressure drop;

Beginning of "constant slope";

The end of the pump movement;

Midpoint of pressure rise; and,

The end of the aspiration process.

Figure 4:
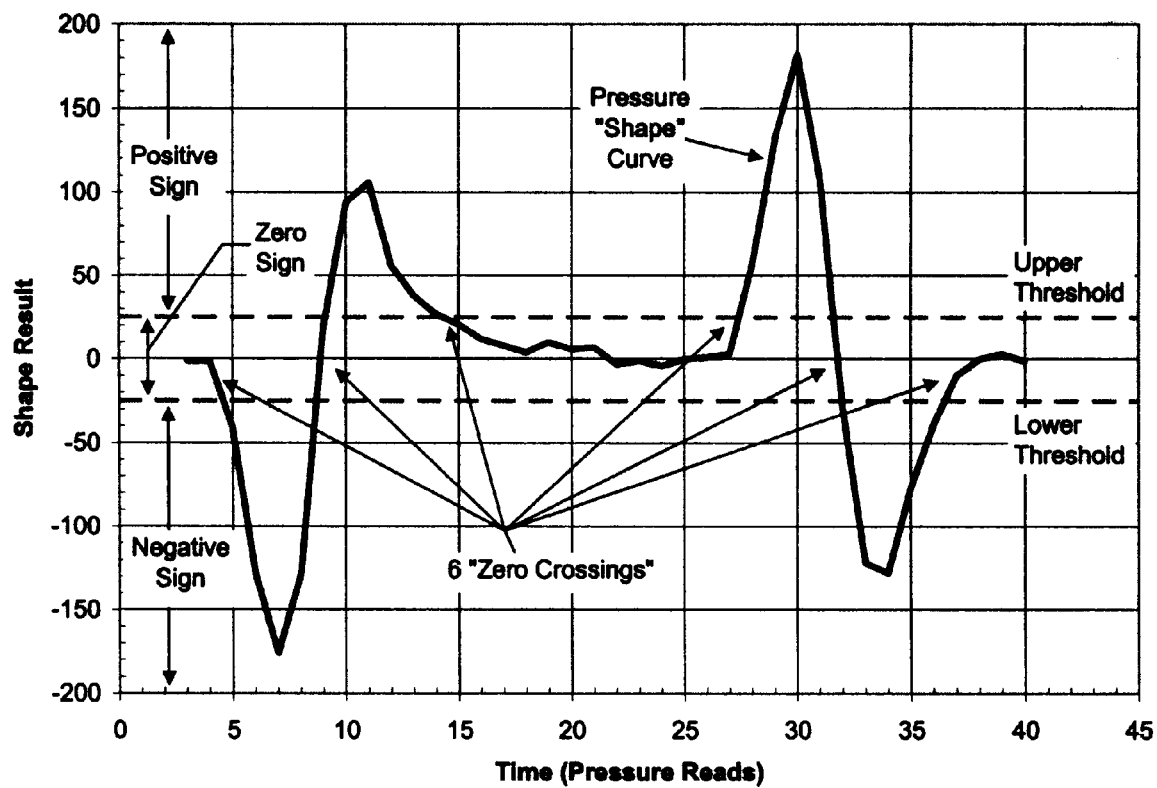
FIG. 4 is a graphical representation of an analysis using the flow diagram of FIG. 3.

If additional peaks or valleys (due to sudden changes in aspiration rate) are present in the curve, they will show up as additional inflection points. The inflection points can be found by first calculating the second derivative of the pressure curve, filtering out the "noise" in the points that lie near zero, and counting the number of times the values cross through at least one of two predetermined values, indicated as Upper and Lower Thresholds in FIG. 4. The second derivative shape curve may be obtained using a central difference equation (for example, based on a Taylor series expansion about a point x). The shape of the pressure curve is calculated for a given point x using the numerical value of the pressure h points ahead and h points behind the desired point. Thus, h may be referred to as the "shape span". The "correct" value for h is a function of the sampling rate and the expected rate of change of the pressure signal, and is usually determined empirically. It, in essence, controls the "smoothing" of the shape curve.

Figure 3:
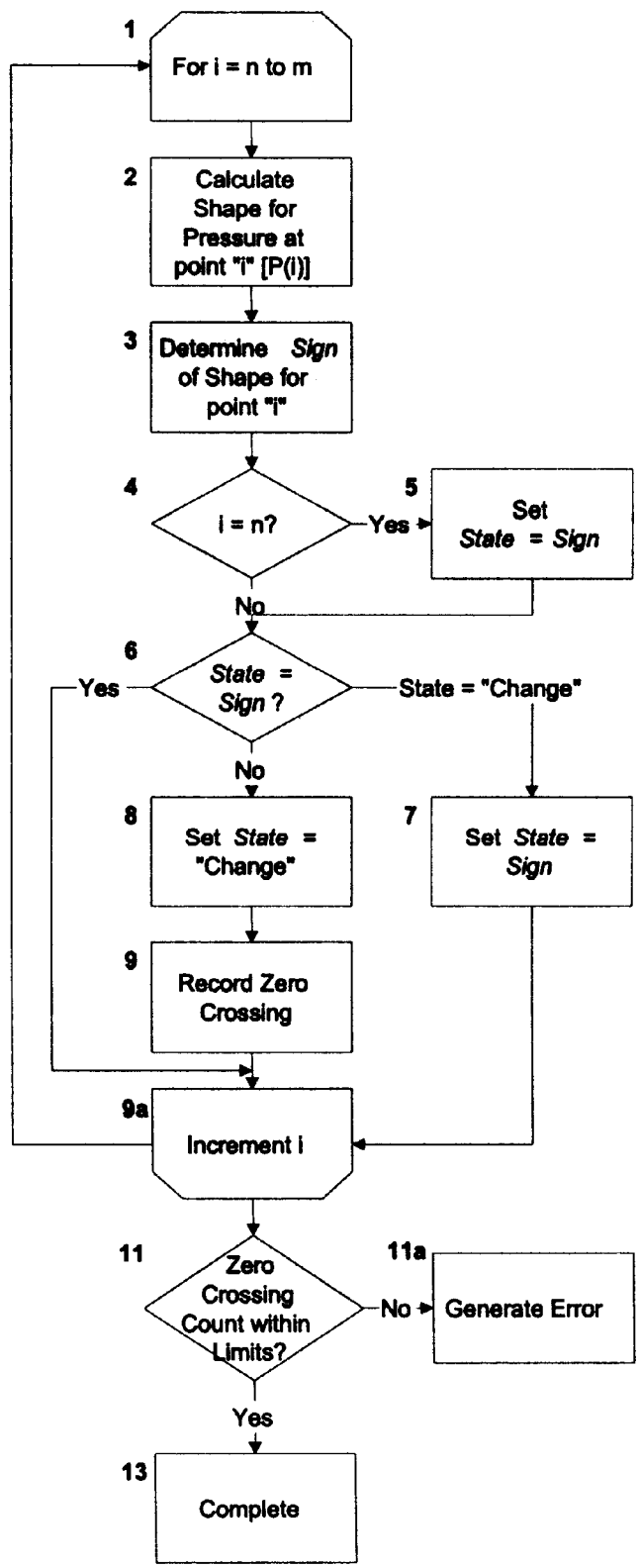
FIG. 3 is a flow diagram describing a aspiration pressure shape test for the aspiration system of FIG. 1.

Filtering of the 2nd derivative pressure shape curve is accomplished by first assuming any value that is within a certain distance (threshold) of zero is zero. A point is then determined as an inflection point if both the sign of the preceding point (+, −, or zero) is not equal to the sign of the current point, and if the preceding point is not an inflection point. This filtering algorithm is illustrated in FIG. 3 wherein in Step 1, the algorithm loops through each point for which the second derivative can be calculated (those points which are a distance of "Shape Span" (i.e., h) from the edges). The shape function is calculated in Step 2, and the sign of the result is determined in Step 3. A result of the shape calculation may have one of three signs: positive, negative, or zero. A Positive sign is assigned if the result is larger than the upper "Shape Threshold" limit, a Negative sign is assigned if the result is below the lower "Shape Threshold" limit, and a sign of "Zero" is assigned if the result is between the "Shape Threshold" limits (See FIG. 4).

Steps 4 and 5 initialize the algorithm for the first point calculated, since no previous point exists for the comparison to be performed in the subsequent steps. The remainder of the algorithm is a state machine comprised of four states: Positive, Negative, Zero, and Change. The current sign is compared with the current state in Step 6, and if they are the same, the algorithm moves on to the next point. If the current state is not equal to the current sign, then the state is reset to "Change" in Step 8, and a "Zero Crossing" is recorded in Step 9, and then the algorithm moves on to the next point. If the current state is "Change", then the state is reset to the current Sign in Step 7, prior to moving on to the next point.

Once all of the points have been filtered through the algorithm, the number of "Zero Crossings" is summed and compared a predetermined count in Step 11. If the number of "Zero Crossings" does not match the predetermined count, an error is declared in Step 12.

In this exemplary embodiment, the equation for Pressure 2nd Derivative, at a single point x, was calculated using a commercial LabView application, available from National Instruments, Austin, Tex., pressure data and is shown as Eq. 1 below with "h" set to 120 ms; i.e., the slope for a point "x" is calculated based on the pressure values of the points 120 ms ahead and 120 ms behind it. By setting the threshold at ±25 A/D, the shape curve touches or crosses zero six times. Such a calculation may also be made using a conventional spreadsheet application or may be integrated into the operational system software of the aspiration system 10 as controlled by computer 24.

$$P''(x)=[P(x+h)-2P(x)+P(x+h)]/h^2 \qquad \text{Eq. 1}$$

Since the pressures are values from the A/D converter, and thus are a finite set of integers, the results of the second derivative calculation are a finite set of incremental values. Thus, the denominator may be eliminated for simplicity, as shown in Eq. 2 below.

$$P''(x)=P(x+h)-2P(x)+P(x+h) \qquad \text{Eq. 2}$$

The threshold value for the filtering was determined empirically so that it is larger than the "noise" of the system. Table 1 below shows operating specifications for calculating the pressure shape in this exemplary embodiment of the present invention and FIG. 4 graphically illustrates the Pressure Shape test analysis.

TABLE 1

| Shape Span (h) | 3 reads |
| Shape Threshold | ±25 A/D counts |

Pressure Recovery Test

The second pressure recovery test checks for clogs and aspiration of cells by verifying that the pressure in the system has risen back to an equilibrium level at a specified time after stopping of the aspiration pressure control means 30, which is an indication of the viscosity and flow restriction of the fluid in the pipette tip 20. A failure in this test will indicate that either the tip 20 is partially clogged, or that the tip 20 is aspirating from within the cell layer. The test begins measuring the slope of the pressure curve a specified or calculated time after the start of data collection. If any slope reading is outside of the threshold, the test generates a failure.

In a similar manner as described earlier, the slope may be estimated using a central difference equation (for example, based on a Taylor series expansion about a point x). The slope of the pressure curve is again calculated for a given point x using the numerical value of the pressure h points ahead and h points behind the desired point. In this instance, h may be referred to as the "slope span". The "correct" value for h is a function of the sampling rate and the expected rate of change of the pressure signal, and is usually determined empirically. It, in essence, controls the "smoothing" of the slope curve.

The equation for the pressure slope at a single point x is determined using Eq. 3 below.

$$P'(x)=[P(x+h)-P(x-h)]/2h \qquad \text{Eq. 3}$$

As with the pressure shape test, since the pressure readings are from an A/D converter within pressure sense device 28 and are thus integers, the results of the slope calculation are a finite set of incremental values. Since "h" is a constant, and since it is the relative value, not the actual value, of the slope that is important, the calculation may be simplified by eliminating the denominator in Eq. 3, making the results a finite set of integers, illustrated by Eq. 4 below.

$$P'(x)=P(x+h)-P(x-h) \qquad \text{Eq. 4}$$

The threshold limit for the recovery test is determined empirically to allow for the aspiration of reasonably viscous samples. Samples with larger viscosity's than about 15 times that of water will saturate the pressure sense device 28, and thus the slope at that point was the chosen threshold. The first slope read point was chosen to maximize the measured difference between "good" and "bad" aspirations.

Figure 5:
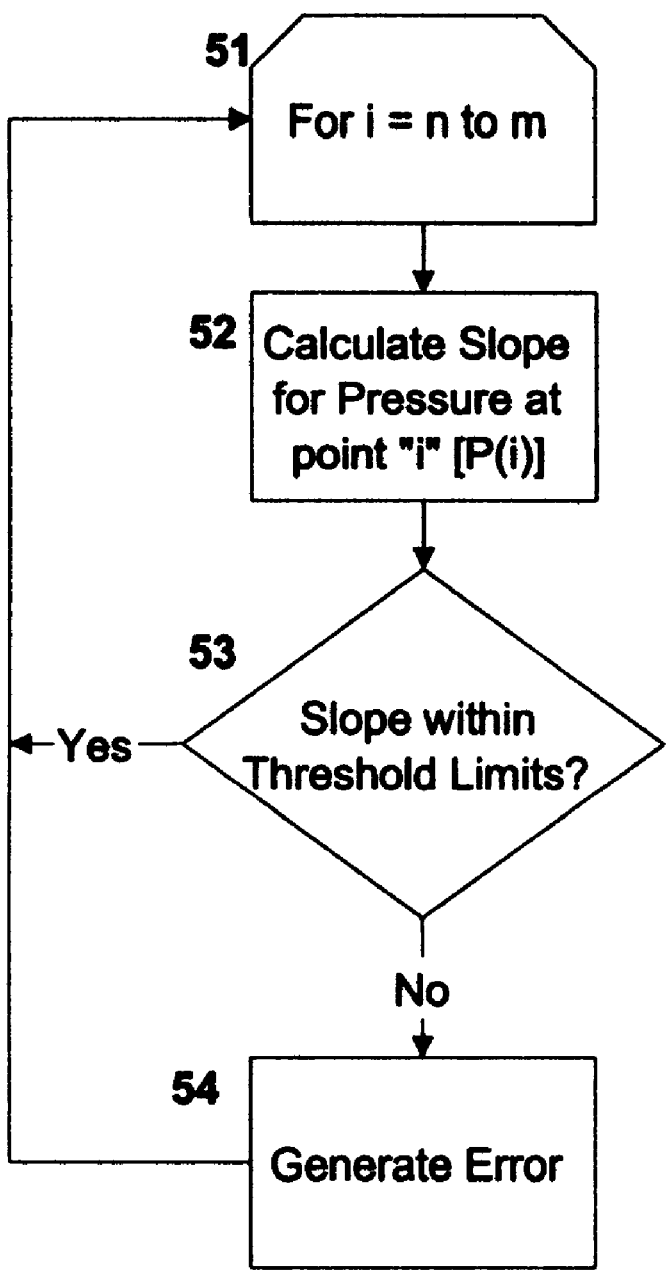
FIG. 5 is a flow diagram describing a aspiration pressure recovery test for the aspiration system of FIG. 1.

FIG. 5 illustrates the algorithm useful in performing the Pressure Recovery test. The algorithm loops through each data point, starting in Step 51 from a predetermined (or calculated) "Equilibrium Point" through the final data point in the data set for which the slope can be calculated (a distance of the Slope Span, or h, from the end of the data set). At each point the slope is calculated, Step 52, and in Step 53 is compared to the upper and lower "Slope Threshold" limits. If the slope is outside of the limits, an error is issued, Step 54, otherwise, the loop continues through the remaining points.

Table 2 below shows operating specifications for calculating the pressure difference in this exemplary embodiment of the present invention.

TABLE 2

| Slope Span (h) | 1 read |
| Slope Threshold | ±32 A/D counts |
| First data point at which slope is calculated | 38$^{th}$ A/D read |

Pressure Difference Test

By inspection of FIG. 2, it is noted that the first aspiration pressure difference test verifies that the difference in pressure between pre-aspiration and post-aspiration falls within specified limits, an indication that the proper amount of sample has been aspirated. The pressure difference is a measure of the head pressure of the fluid 14 in the pipette tip 20. A failure in this test will indicate that either too much or too little sample has been aspirated. Its primary purpose is to determine if a large volume of air has been aspirated, or if a large clog occurred during aspiration.

Figure 6:
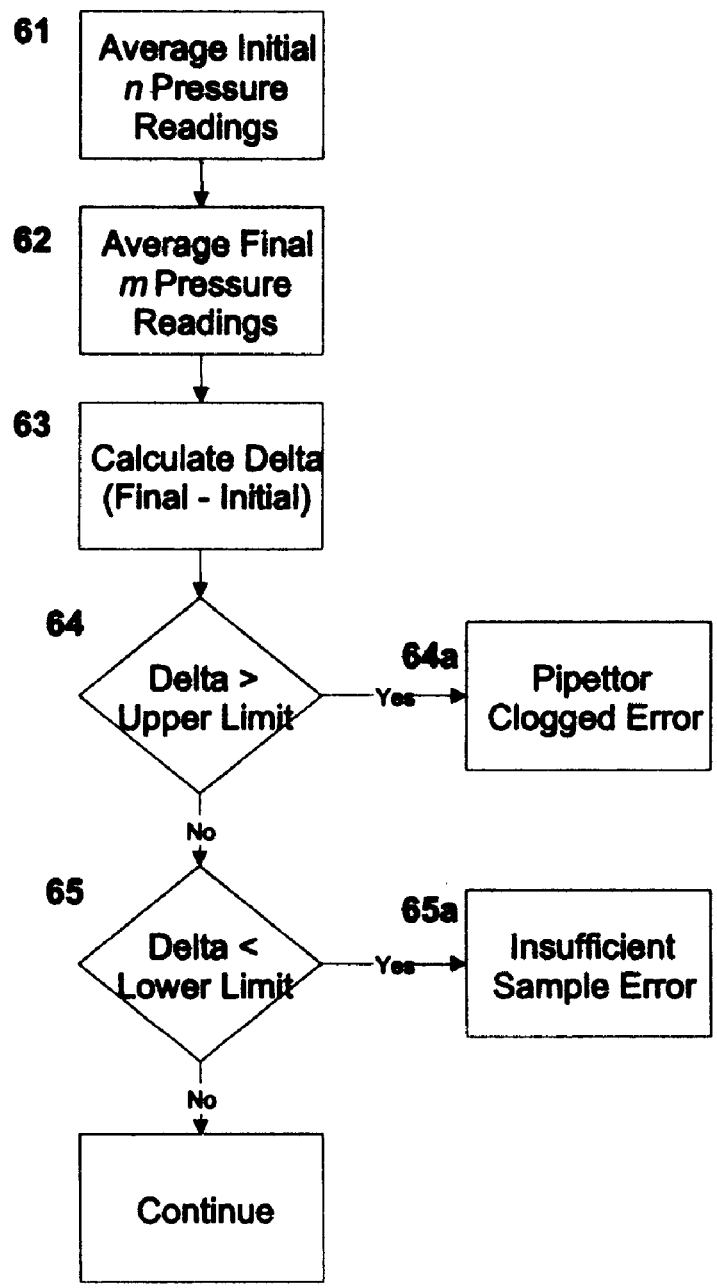
FIG. 6 is a flow diagram describing a aspiration pressure difference test for the aspiration system of FIG. 1.

FIG. 6 is illustrative of steps taken during the Pressure Difference test. In Step 61, an average of multiple pressure readings is taken prior to pump aspiration start. In Step 62, a second average is taken a specified later time (sufficient enough for the pressure to reach a steady state after a normal aspiration). In Step 63, the difference between the second average and the first average is the pressure delta. In Step 64, if the calculated difference is larger than a predetermined or calculated upper limit, a "Clogged Pipettor" error is issued by system computer 24. In Step 65, if the difference is less than a predetermined or calculated lower limit, then an "Insufficient Sample" error is issued by system computer 24. Alternately, if either error condition is detected, the system computer 24 may act to prevent a transfer of the liquid aspirated from the pipette to any places external to the pipette.

The equation 5 shown below may be used to calculate the pressure difference:

$$\Delta P=P_{2avg}-P_{1avg} \qquad \text{Eq. 5}$$

The limits for the difference test are chosen to be wide enough to cover variations between various analyzers, which does not present any difficulties because this method is intended to detect gross aspiration errors. Table 3 below shows operating specifications for calculating the pressure difference in an exemplary embodiment of the present invention.

TABLE 3

| Number of Points in Average | 8 ± 1 |
|---|---|
| Data point at which second average begins | 38 |
| Max Pressure Delta | −300 A/D counts (−0.097 psi) |
| Min Pressure Delta | −180 A/D counts (−0.058 psi) |

As might be anticipated by one skilled in the art, increasing viscosity of the aspirated sample increases the "time constant" of the system, i.e. the time for the pressure to recover to its final value after aspiration is complete, as seen in FIG. 2. Data for FIG. 2 were obtained at the output of the pressure sense device 28 by the LabView application with a sampling rate of 2000 Hz. In comparing, for example horse plasma and whole horse blood to glycerol, it is discovered that the plasma has a viscosity of between 1.2 to 2.0 cps, and the whole blood has a viscosity of about 5.0 cps. Viscosity's larger than about 15 cps cause the pressure transducer to saturate.

Pressure data collected by the pressure sense device 28 with the LabView application may be converted to 10-bit A/D readings by first reducing the sampling rate to 25 Hz, and then multiplying the voltage by 204.8 Volts per A/D count (5V/1024 A/D counts=204.8). This conversion may be verified by comparing converted LabView data with any computer-assisted method for determining arithmetic derivatives using conventional software calculations.

The pressure data are collected in real time throughout the aspiration cycle. The analog input subsystem reads the pressure sense device 28 at a constant rate (for example 25 Hz) time stamping each reading and buffering the reading(s) for eventual inclusion into the aspiration data set. In parallel to the aspiration cycle this pressure data is periodically transferred from the analog sub-system buffer into the aspiration data set. The aspiration data set consists of a series of time stamped pressure readings that occur before during and after the pump operation. Each process event (start of aspiration cycle, start of pump cycle, end of pump cycle & end of aspiration cycle) is marked in the data set. To achieve close coupling with process events the data is also read from the analog sub-system coincident with these events. The resultant aspiration data set contains a multiple of time stamped pressure and event markers that allow analysis of the aspirations success.

Leak Detection Test If an air leak is present in the liquid aspiration system 10, a partial vacuum cannot be maintained, and thus aspirated fluid may leak out of the pipettor 12 during the time between the completion of sample aspiration and the sample dispense. This condition may contaminate the analyzer or may cross-contaminate samples. Therefore detection of the existence of a leak condition is highly desirable.

As with an aspiration or dispense, the pressure within the liquid aspiration system 10 is continuously monitored to verify that it has the characteristics of a nominal leak-free system (or, conversely, to detect the characteristics of a leak). Thus the same three algorithms which are used in the Aspiration Quality Determination (Pressure Delta, Pressure Recovery, and Pressure Shape) are used for leak detection as well.

The pressure in a leak-free liquid aspiration system 10 remains relatively constant between the completion of the aspiration and the beginning of the dispense sequences. However, the specific value of this constant pressure is dependent on many factors, including the volume of fluid aspirated. Thus a simple check on the value of this pressure is insufficient to determine if an unwanted leak is present.

Figure 7:
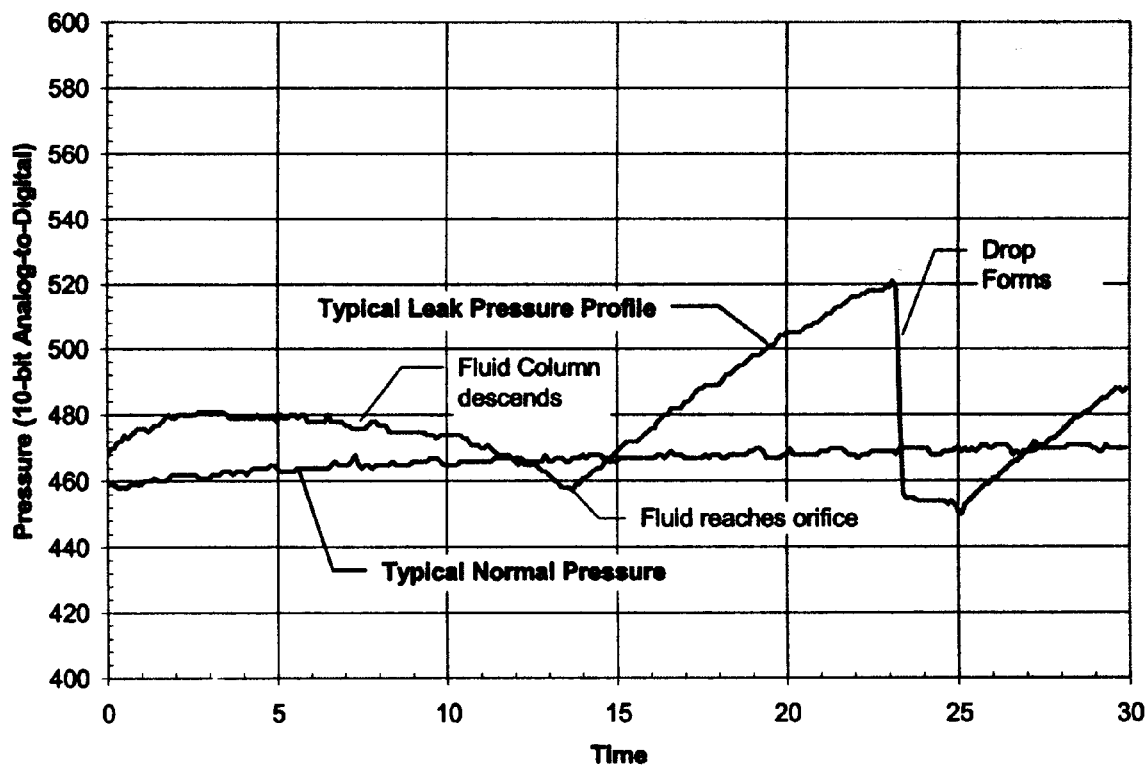
FIG. 7 is a comparison of pressure profiles in a system with and without an air leak; and, FIG. 8 is a shape calculation for the system of FIG. 7.

In this exemplary embodiment of the liquid aspiration system 10 to detect the presence of an air leak, the fluid sample is held within the pipettor 12 for a period of time that can range up to 15 seconds. This fluid sample is held approximately ¼" above the orifice of the pipettor 12. If an air leak is present in the liquid aspiration system 10, the liquid column in pipettor 12 moves downwards until it reaches the orifice. During this time, the pressure in the liquid aspiration system 10 fluctuates; specifically, it rises and then falls again as the fluid descends through the narrow portion of the pipette tip, as illustrated in FIG. 7. Once the fluid column reaches the orifice, fluidic forces (surface tension, etc.) restrain the fluid from moving further. As air continues to leak into the liquid aspiration system 10, the pressure increases. Eventually, this pressure overcomes the fluidic forces, and a droplet forms outside of the pipette tip. As the droplet forms, pressure in the system falls rapidly (as a result of the increase in air volume, which is equal to the volume of the drop that is now outside of the system). With air continuing to enter the system, the droplet grows larger while the pressure remains constant. Finally, the droplet detaches from the pipettor 12, the fluidic forces again restrain the fluid column, and pressure begins to increase again. This saw-tooth pattern continues to repeat itself.

This pattern is detected by applying the same algorithms as described earlier, using different parameters. Data collection is accomplished using the same system that collects data for the aspiration and dispense processes. The algorithms are also employed during the data collection, for early detection and to minimize the consequences of a leaking pipettor 12.

The Pressure Delta algorithm is utilized to compare the current pressure to the pressure at the end of aspiration to detect very large leaks (such as a pipettor 12 tip falling off).

Figure 8:
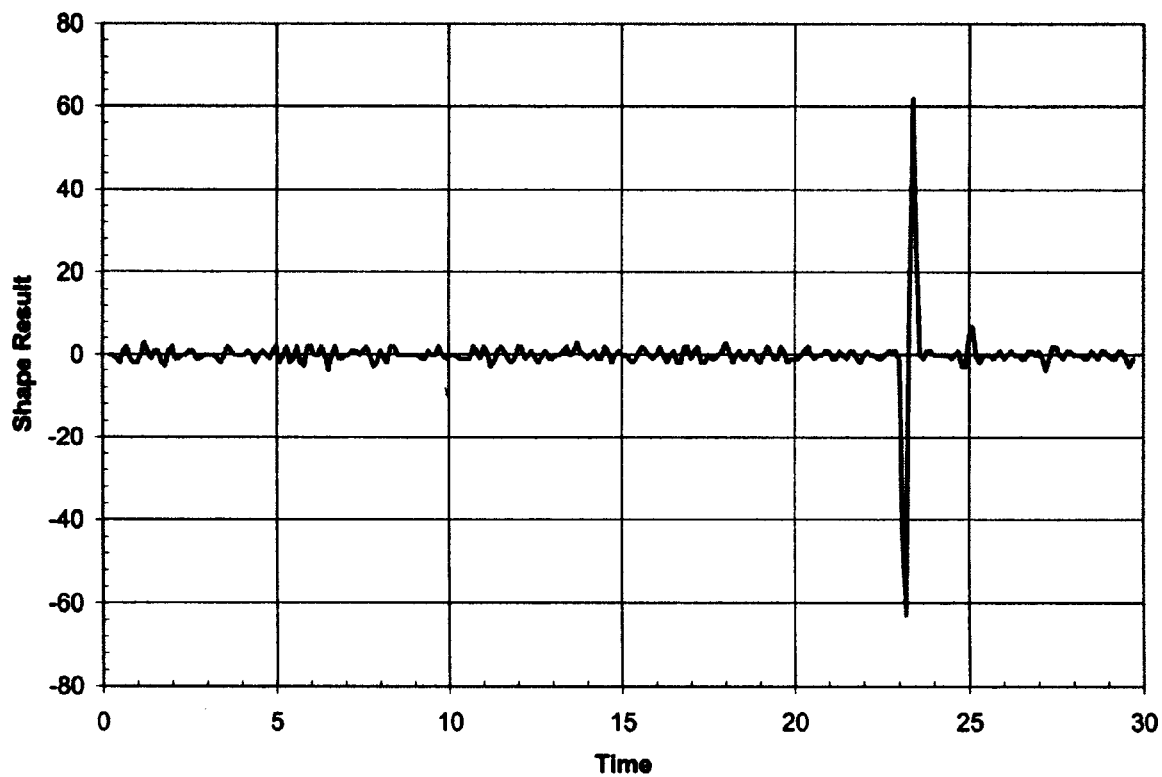

The Pressure Shape (rate of change of the slope) is calculated for the entire set of pressure readings to detect the sudden drop in pressure as a droplet forms. The time span h used for this calculation is relatively small, to provide the quickest response time to a falling droplet. Normally, in the absence of an air leak, the result of the calculation is near zero. However, if a droplet falls from the tip, the calculation produces a much larger value, as shown in FIG. 8 for the pressure curves in FIG. 7. When this value exceeds a predetermined threshold value, a leak is declared and the appropriate response is taken. Thus, the number of "zero-crossings" allowed for this shape test is zero.

The Pressure Slope calculation may be used in place of the Pressure Shape calculation for essentially the same result. In this embodiment, the Pressure Slope calculation is used over a longer time span h to detect the early pressure fluctuations as the fluid column descends toward the orifice. The longer time span is necessary to detect this relatively slow event (seconds as opposed to the tenths of seconds it takes to form a drop). Detection of this event allows the leak to be declared before a drop forms, which provides time to respond before contamination can occur. Again, a predetermined threshold larger than zero is set, and if the calculation result exceeds this threshold, a leak error is declared. This test alone is not sufficient to detect all leaks, however; a fast drop-formation may be missed, thus the need for the high-rate tests described in the previous paragraphs. Table 4 below shows operating specifications for determining the presence of an air leak in an exemplary embodiment of the present invention.

TABLE 4

| | |
|---|---|
| Pressure Delta Test | >100 |
| Shape Span (h) | 5 reads (0.2 sec) |
| Shape Threshold | ±10 |
| Number of Zero Crossings | 0 |
| Slope Span (h) | 25 reads (1 sec) |
| Slope threshold, low | −5 |
| Slope threshold, high | 8 |

Those skilled in the art will appreciate that the embodiments of the invention disclosed herein are illustrative of the principles of the invention and that other modifications may be employed which are still within the scope of the invention. For example, obvious variants of the invention should also be applicable to a fluid-coupled system with a few adjustments to the parameters. The method also could be applied to the fluid dispensing process to determine success of the dispense operation. The method could also be adjusted to distinguish between fluid types; for example, normal serum from whole blood. Given the known relationship between sample volume and pump displacement, the method could also be used to aspirate a variable volume. Accordingly, the present invention is not limited to those embodiments precisely shown and described in the specification but only by the following claims.

What is claimed is:

1. A method for determining the quality of an aspiration process during which liquid is aspirated between a container and a pipette comprising the steps of:
   determining with a pressure sensing device the shape of a pressure curve representative of aspiration pressure within the pipette;
   verifying that the pressure curve has features that match the features of an acceptable pressure curve by performing an aspiration pressure shape test; and,
   wherein the aspiration pressure shape test verifies that the rate of change in the of the slope of the pressure curve crosses at least one of two predetermined values a predetermined number of times.

2. The method of claim 1 wherein the predetermined values are upper and lower threshold values selected to be relatively insensitive to minor variations in the pressure curve.

3. The method of claim 1 wherein the rate of change of the slope of the pressure curve is determined by calculating the second derivative of the pressure curve and is calculated for a given point x using the numerical value of the aspiration pressure h points ahead and h points behind the point x.

4. The method of claim 1 wherein the predetermined number of times is equal to six.

* * * * *